(12) United States Patent
Tirronen et al.

(10) Patent No.: US 9,073,847 B2
(45) Date of Patent: Jul. 7, 2015

(54) METHOD AND AN ARRANGEMENT FOR SEPARATING AT LEAST ONE CARBOXYLIC ACID AND FURFURAL FROM A DILUTE AQUEOUS MIXTURE THEREOF

(71) Applicant: TAMINCO FINLAND OY, Oulu (FI)

(72) Inventors: Esko Tirronen, Espoo (FI); Antero Laitinen, Kirkkonummi (FI); Jukka Hietala, Porvoo (FI)

(73) Assignee: TAMINCO FINLAND, Oulu (FI)

( * ) Notice: Subject to any disclaimer, the term of this patent is extended or adjusted under 35 U.S.C. 154(b) by 0 days.

(21) Appl. No.: 14/355,629

(22) PCT Filed: Nov. 2, 2012

(86) PCT No.: PCT/FI2012/051072
§ 371 (c)(1),
(2) Date: May 1, 2014

(87) PCT Pub. No.: WO2013/064751
PCT Pub. Date: May 10, 2013

(65) Prior Publication Data
US 2014/0275581 A1    Sep. 18, 2014

(30) Foreign Application Priority Data

Nov. 4, 2011   (FI) .................................... 20116091

(51) Int. Cl.
| C07D 307/50 | (2006.01) |
| C07C 51/46 | (2006.01) |
| B01D 11/04 | (2006.01) |
| C07C 51/48 | (2006.01) |
| C07C 51/44 | (2006.01) |
| C07D 307/48 | (2006.01) |

(52) U.S. Cl.
CPC ............ C07C 51/46 (2013.01); B01D 11/0434 (2013.01); B01D 11/0492 (2013.01); C07D 307/50 (2013.01); C07C 51/48 (2013.01); C07C 51/44 (2013.01); C07D 307/48 (2013.01)

(58) Field of Classification Search
CPC ....................................................... C07C 51/46
USPC ............................................................ 549/490
See application file for complete search history.

(56) References Cited

U.S. PATENT DOCUMENTS

2011/0071306 A1    3/2011   Robinson

FOREIGN PATENT DOCUMENTS

| AT | 356 509 B | 5/1980 |
| EP | 0 111 699 A1 | 6/1984 |
| FR | 942 094 A | 1/1949 |
| GB | 749 696 A | 5/1956 |
| WO | 2009/130386 A1 | 10/2009 |
| WO | 2011/063500 A1 | 6/2011 |
| WO | 2011/161141 A1 | 12/2011 |

OTHER PUBLICATIONS

International Search Report of PCT/FI2012/051072 dated Mar. 8, 2013.
Xing et al., "Production of furfural and carboxylic acids from waste aqueous hemicellulose solutions from the pulp and paper and cellulosic ethanol industries.," Energy & Environmental Science, 2011, pp. 2193-2205, vol. 4.
Finnish Search Report issued in Finnish Application No. 20116091 dated Sep. 20, 2012.
Finnish Office Action issued in Finnish Application No. 20116091 dated Sep. 20, 2012.

*Primary Examiner* — Taofiq A Solola
(74) *Attorney, Agent, or Firm* — Sughrue Mion, PLLC

(57) ABSTRACT

The present invention relates to a method and an arrangement for separation and recovery of at least one carboxylic acid and furfural from a dilute aqueous mixture thereof. In the method of the present invention a dilute aqueous mixture comprising at least one carboxylic acid and furfural is extracted with methyltetrahydrofurane, and at least one carboxylic acid and furfural are recovered. The arrangement of the present invention comprises an extraction unit 302 for carrying out extraction of at least one carboxylic acid and furfural from dilute aqueous mixture with methyltetrahydrofuran, connected to distillation unit 307 for carrying out distillation of the extract 305 from the extraction unit 302, and connected to acids distillation unit 320 for carrying out distillation of the bottom stream 308 from the distillation unit 307 to separate at least one carboxylic acid and furfural.

23 Claims, 3 Drawing Sheets

METHOD AND AN ARRANGEMENT FOR SEPARATING AT LEAST ONE CARBOXYLIC ACID AND FURFURAL FROM A DILUTE AQUEOUS MIXTURE THEREOF

FIELD OF THE INVENTION

The present invention relates to a method and an arrangement for separating and recovering organic acid(s) and furfural from a dilute aqueous mixture thereof wherein the amounts of organic acid(s) and furfural are low. In particular, the method and the arrangement relate to separation and recovery of concentrated carboxylic acid(s) and furfural from their dilute aqueous mixture.

BACKGROUND OF THE INVENTION

Several industrial scale processes such as biomass degradation are known to produce dilute aqueous solutions comprising low amounts of furfural and organic acids such as carboxylic acids. Due to environmental reasons recovery of furfural and organic acids has become increasingly interesting. These economically valuable by-products have typically been recovered by distillation or extractive distillation, which are effective but energy consuming and technically challenging processes due to formation of azeotropes or stable emulsions rendering processing uneconomical or providing the product in an undesirable form, such as too dilute solution, which is difficult to use in further processes.

Separation of various chemicals may be based on liquid-liquid extraction processes. Even carboxylic acids have been separated from dilute aqueous solutions with extraction solvents insoluble or slightly soluble in water, or with solvent mixtures. However, the efficiency of extraction agents is typically not satisfactory enough to yield pure components or the extractant binds an acid so strongly that recovery of the acid becomes difficult.

Carboxylic acids and furfural are formed as products in various biomass hydrolysis processes. Economical recovery of these components from typically dilute water mixture obtainable from these processes involves liquid-liquid extraction as a first stage followed by multiple distillation units to recycle extraction solvent and separate extracted components as pure products. Both physical and reactive solvents as well as their combinations have been used to extract carboxylic acids and furfural. The published single extraction solvent systems for these compounds either extract carboxylic acids with good yield or extract furfural but have not been able to extract both types of chemicals simultaneously in good yield without side effects. Physical extraction solvents like hydrocarbons, ketones and esters have usually unfavourable extraction yield for formic acid. Reactive extraction solvents, such as trialkyl amines, are typically specific for carboxylic acids but extraction of furfural and separation of acids from strong amine-acid complexes as an additional phase are problematic. Trialkyl phosphine oxides, e.g. Cyanex 923, are good extraction chemicals for carboxylic acids and furfural but the formed complex with acids, especially with formic acid, is strong and needs separation by distillation.

U.S. Pat. No. 2,437,519 discloses extraction of lower aliphatic acids such as formic acid and acetic acid from dilute aqueous solutions using tetrahydrofurane (THF) or its derivatives, such as 2-methyltetrahydrofurane (2-MTHF), as the extracting solvent. U.S. Pat. No. 2,437,519 further teaches that it is preferred to add to the solvent an amount of a third substance, practically insoluble in water, for instance a hydrocarbon like benzene, to reduce the amount of water dissolved in the aqueous layer of the extracting solvent and acid. The concentration of extracted acid is thus increased and the solubility of the extracting solvent in the aqueous layer is reduced. The extract that is obtained is treated according to any known methods for recovering therefrom its acid content in anhydrous conditions. It may be subjected, for instance, to a distillation during which azeotropic dehydration of the extract takes place with the extracting solvent playing the part as a water entrainer and being separated from the anhydrous acid. The document, however, does not discuss mixtures including other organic compounds, such as furfural.

The applicant's former patent application WO 2009/130387 relates to a process for the recovery of formate salt from biomass. An aqueous liquid mixture containing levulinic acid, formic acid and possibly furfural is subjected to a liquid-liquid extraction step, followed by recovery of furfural, formate salt and levulinic acid or levulinic salt. In the disclosed process a mixture containing formic acid and levulinic acid and optionally furfural is (i) subjected to liquid-liquid extraction by employing an extracting agent whereby an organic phase comprising the extracting agent, formic acid, levulinic acid and optionally furfural, and an aqueous phase comprising essentially water, preferably further containing inorganic acid(s), are obtained; (ii) optionally, furfural is separated and recovered, preferably by distillation and gravitational separation, from the organic phase; (iii) formic acid is recovered by distillation as concentrated acid from the organic phase. The organic phase contains formic acid and levulinic acid from step (i) or optionally from step (ii); and (iv) levulinic acid is recovered from the organic phase. Preferred extracting agents are tertiary amines, secondary or tertiary amides, tertiary phosphine oxides, tertiary phosphates, $C_5$-$C_{12}$ fatty acids, $C_8$-$C_{12}$ fatty alcohols and alkyl urea derivatives.

The reactive extraction solvents e.g. trialkyl amines of WO 2009/130387 are typically specific for carboxylic acids but their ability to extract furfural depends on feed pH and they form very strong amine-formic acid complexes. Often these complexes separate as second organic phase. Trialkyl phosphine oxides, such as Cyanex 923, are good extraction chemicals for carboxylic acids and furfural but the formed complex with acids, especially with formic acid, is strong and has to be separated by distillation.

The separation of valuable compounds such as organic acids and furfural from biomass processes has been achieved by evaporation of furfural-water mixture and treatment of the acid containing aqueous waste either with an extraction or with a distillation entreiner. These treatments work usually much better with acetic acid than with formic acid.

An article by Xing R., et al. "Production of furfural and carboxylic acids from waste aqueous hemicellulose solutions from the pulp and paper and cellulosic ethanol industries", Energy Environ. Sci., 2011, 4, 2193 discloses a process to produce furfural and co-products of formic and acetic acids from waste aqueous hemicellulose solutions using a continuous two zone biphasic reactor. Furfural is produced in a two-step process consisting of hydrolysis of xylose oligomers followed by the dehydration of xylose monomers and then extraction of the furfural into an organic solvent. The aqueous hemicellulose solution (aqueous phase) is saturated with sodiumchloride (NaCl). In the process NaCl-pretreated tetrahydrofuran (THF) is primarily used as the organic phase due to its great affinity for furfural, low boiling point, and ease of separation from water.

THF is pretreated with NaCl, because pure THF is totally soluble in water. For the same reason the aqueous phase is saturated with NaCl. Addition of NaCl does not improve THF as an extractant but it helps in the separation of the phases by salting out. The use of NaCl in an extraction of industrial scale is however not economically viable. The reuse and disposal of the formed salt solution with traces of water-miscible organic components becomes complicated.

As disclosed above there is a need for a more economical and efficient process to separate and recover carboxylic acid(s) and furfural simultaneously from a dilute aqueous mixture with a single extraction solvent.

SUMMARY OF THE INVENTION

The object of the present invention is to provide an efficient method for separating and recovering carboxylic acid(s) and furfural from a dilute aqueous mixture.

A further object of the present invention is to obtain carboxylic acid(s) and furfural as concentrated compound(s) with good extraction and overall yield.

Yet, a further object of the present invention is to separate and recover carboxylic acid(s) and furfural with extraction by using a single extractant.

Yet, a further object of the present invention is to separate and recover carboxylic acid(s) and furfural simultaneously with extraction by using a single extractant.

Yet, a further object of the present invention is to provide an arrangement to separate and recover carboxylic acid(s) and furfural simultaneously with extraction by using a single extractant.

The present invention is directed to provide a solution to the above mentioned problems. The inventors have surprisingly found that a mixture containing at least one organic acid such as carboxylic acid and furfural can be efficiently extracted with methyltetrahydrofuran, such as 2-methyltetrahydrofuran, and the valuable components can be separated simultaneously from a dilute aqueous mixture thereof.

The overall process is economical and efficient as the carboxylic acid(s) and furfural separation is facilitated and the process provides high carboxylic acid(s) and furfural extraction yields and overall yield. In addition to the advantage of having good extraction properties the used extractant provides a sharp interface between the organic phase and aqueous phase resulting in minimum amount of mixed phase dispersion such as emulsion. The used light solvent is easily separable from the extract by e.g. distillation. It is able to form an azeotrope with water enhancing residual water removal from the organic acid(s)-furfural mixture. Furthermore, recycling of the used extracting solvent is facilitated.

DETAILED DESCRIPTION OF THE INVENTION

Figure 1:
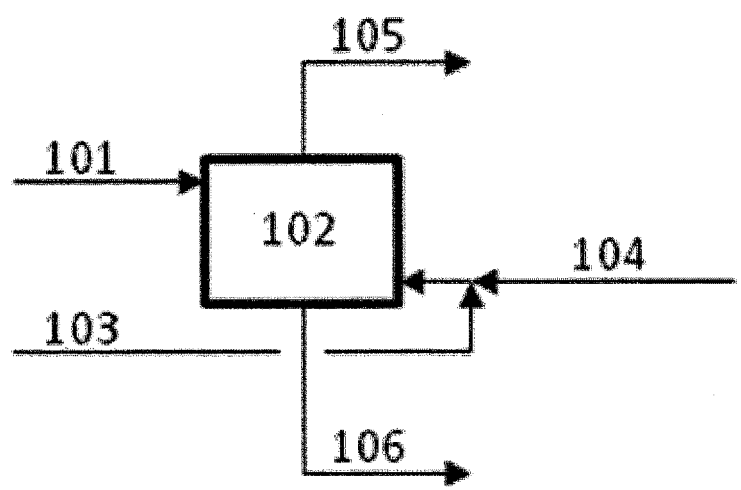
FIG. 1 is a schematic layout set up for an arrangement suitable for use according to the method of the present invention where formic acid, acetic acid and furfural are simultaneously separated and subsequently recovered from a dilute aqueous mixture thereof.

In the present invention by the term "extract" is meant the composition formed after extracting comprising the extracting agent and the valuable compounds to be recovered i.e. carboxylic acid(s) and furfural in this case.

By the term "extractant" or "extracting solvent" is meant the extracting agent.

By the term "raffinate" is meant the residual aqueous phase after extraction.

An aqueous mixture containing carboxylic acids and furfural may originate from biomass processing i.e. from processes used in treatment of pulp, waste paper, paper mill sludge, agricultural residue, rice straws, woody plant, cotton materials or cellulose fine from papermaking or any biomaterial. Preferably, the mixture containing carboxylic acid(s) and furfural is obtained by hydrolysis of biomass. This hydrolysis process is typical for producing levulinic acid and esters thereof. Preferably, the dilute aqueous mixture originates from biomass, preferably from biomass acidic hydrolysis process, most preferably from biomass acidic hydrolysis process to produce levulinic acid and/or esters thereof.

In a preferred embodiment the dilute aqueous mixture originates from biomass acidic hydrolysis process and is distilled and condensated at least once in order to provide reproducible quality for the feed. The fluctuations in quality due to varying origin of the biomass such as use of hardwood instead of softwood would otherwise render processing too complicated.

By the term "mixture" is meant an aqueous liquid mixture suitable for liquid extraction by conventional extraction means allowing the presence of some solids, preferably less than 5%, more preferably less than 1% by weight, wherein the amount of solids is low enough for not disturbing the extraction process. The dilute aqueous mixture may further comprise impurities such as light water soluble polar compounds and/or light hydrocarbons.

The dilute aqueous mixture of the present invention comprises at least one carboxylic acid, preferably lower aliphatic carboxylic acid, or mixtures of several carboxylic acids. The acid is most preferably selected from the group of formic acid and acetic acid or a mixture thereof.

The concentration of the carboxylic acids in total in the dilute aqueous mixture is less than 40% by weight, preferably less than 20% by weight. An especially economically feasible concentration of the mixture is most preferably less than 15%, such as less than 10%, when compared to other separation methods. Depending on the previous processing steps the concentration may be even much lower, preferably from 0.1 to 10% by weight, most preferably from 0.5 to 5% by weight such as from 1 to 4%. The concentration of acetic acid may be less than 1%, more preferably less than 0.1% or even as low as about 0.01% by weight. Acetic acid is formed in the degradation of hemicellulose through pentosan sugar fraction. The major portion of the carboxylic acid content is typically formic acid and the minor portion is acetic acid. The furfural concentration of the dilute aqueous mixture is less than 40% by weight, preferably less than 15% by weight more preferably from 0.01 to 10% by weight, most preferably from 0.5 to 5% by weight, such as from 1 to 4% by weight.

In the first aspect of the present invention a method is provided for separating at least one carboxylic acid and furfural simultaneously from a dilute aqueous mixture. This method comprises the steps of subjecting the dilute aqueous mixture, comprising at least one carboxylic acid and furfural, preferably comprising formic acid, furfural and optionally acetic acid, to extraction with an extracting agent comprising methyltetrahydrofuran or derivatives thereof, forming an extract comprising an organic phase and a raffinate comprising an aqueous phase, and recovering from said extract at least one carboxylic acid and furfural.

Derivatives of methyltetrahydrofuran may comprise monomethyl or dimethyl tetrahydrofurans, preferably 2-methyltetrahydrofuran, 3-methyltetrahydrofuran, 2,2-methyltetrahydrofuran or 2,5-methyltetrahydrofuran. The extracting agent is more preferably 2-methyltetrahydrofuran, most preferably pure and concentrated 2-methyltetrahydrofuran.

Typically, aromatic hydrocarbons are good extractants to furfural but do not extract carboxylic acids, such as formic acid or acetic acid. Water insoluble trialkyl amines having high boiling points are able to extract both carboxylic acids and furfural by forming complexes with the acids. However, they are typically extremely sensitive to the feed composition contrary to methyltetrahydrofuran, such as 2-methyltetrahydrofuran.

Methyltetrahydrofuran or its derivatives, preferably 2-methyltetrahydrofuran, was found to provide the most efficient extracting properties simultaneously to both types of valuable compounds to be extracted, carboxylic acids and furfural by just dissolving these components. The phase separation is excellent and the sharp aqueous-organic interface result in fast separation rate. Therefore, no salting out or sugaring out methods are necessary. Outstanding features of 2-methyltetrahydrofuran are that it aids in water removal by forming heteroazeotrope with water and it is fully regenerable by distillation. Typically, distillation of heavier solvents requires increased thermal energy resulting in gradual degradation of the solvent compositions due to decomposition reactions taking place at higher temperatures. Furthermore, accumulation of furfural polymers or other heavy impurities does not affect methyltetrahydrofuran, such as 2-methyltetrahydrofuran, in a similar manner to the heavier solvents or mixtures thereof by gradually destroying the extractant. The extraction temperature for 2-methyltetrahydrofuran extractant is low, from ambient to slightly elevated temperature, and yet good extracting characteristics are obtained for both types of compounds to be recovered. The extraction efficiency is high, and on the other hand, the solubility of water to extract comprising the extracting agent, carboxylic acid(s) and furfural is low and the solubility of the extracting agent to raffinate is low. The green solvent, 2-methyltetrahydrofuran, can be prepared from furfural.

Preferably, the extraction takes place at a temperature from about 10 to about 80° C., preferably from about 10 to about 70° C., and most preferably from about 20 to about 45° C. A low temperature is preferred in order to avoid increasing the inherent polymerisation tendency of the furfural component. Small extraction temperature variations were found not to have a marked influence in the yield of the desired components to be recovered. The extraction is preferably performed under a pressure of 5 bar, preferably 3 bar, most preferably under ambient pressure.

The mass ratio of the dilute aqueous mixture to the extracting agent, preferably 2-methyltetrahydrofuran, in the feed is preferably from 0.25 to 4.0, preferably from 0.75 to 2.0. The yield of the desired components to be recovered decreases as the amount of water increases.

The extraction is preferably performed in a counter-current operating extraction column, more preferably in a continuously operating counter-current extraction column. The extraction column advantageously comprises several chambers preferably including mixing in each to ensure efficient contact between the components and more controlled concentration separations.

In a preferred embodiment the raffinate from the extraction of formic acid, acetic acid and furfural from a dilute aqueous solution thereof with 2-methyltetrahydrofuran comprises less than 1% by weight of formic acid, acetic acid and furfural each, less than 10% by weight 2-methyltetrahydrofuran the balance being water. Whereas, the extract comprises up to about 5% by weight formic acid, acetic acid and furfural each, less that about 15% water the balance being 2-methyltetrahydrofuran.

In the preferred embodiment wherein the extraction is performed in a counter-current extraction column the yield of formic acid, after the extraction, is more than 70%, acetic acid more than 80% and furfural more than 99% calculated from the extract (organic phase).

In another preferred embodiment the aqueous phase from the extraction step comprising essentially water is subjected to stripping distillation wherein a top stream distillate drawn from top part of the stripper comprising essentially extractant and a bottom stream comprising water are obtained. The bottom stream comprising water can optionally be filtered through active carbon for removing impurities such as water soluble, heavy impurities and impurities that do not get extracted.

In another preferred embodiment after the extraction of formic acid, acetic acid and furfural into the extracting agent, preferably 2-methyltetrahydrofuran, the extract comprising formic acid, acetic acid and furfural is preferably subjected to distillation whereby a distillate which is drawn from top part of a distillation column comprising extractant-water azeotrope and a bottom stream comprising essentially formic acid, acetic acid and furfural are obtained.

Removal of the extraction solvent from the extract by said distillation takes place at a temperature from about 35 to about 110° C., preferably from about 70 to about 80° C., and most preferably from about 70 to about 75° C., such as at about 71-73° C. at ambient pressure, preferably when distilling the 2-methyltetrahydrofuran and water. By said distillation temperature is meant the temperature of the top part of the distillation column.

In a preferred embodiment the bottom stream of the distillation column comprising formic acid, acetic acid and furfural comprises water less than 5% by weight, the extracting agent, preferably 2-methyltetrahydrofuran, less than 0.2% and some polymerised furfural.

In addition to the excellent extraction properties, 2-methyltetrahydrofuran is a light solvent which is easily distilled from the extract having a low heat of evaporation. Furthermore, it forms a hetero azeotrope with water which enhances residual water removal from the heavier acid-furfural mixture. The low boiling point of 2-methyltetrahydrofuran and its water azeotrope aids in depressing the inherent polymerisation tendency of the furfural component.

Optionally, the bottom stream obtained from said distillation comprising essentially formic acid, acetic acid and furfural is subjected to a further distillation whereby a distillate, drawn from top part of distillation column, comprising water and the extracting agent, preferably 2-methyltetrahydrofuran, and a bottom stream comprising formic acid, acetic acid and furfural are obtained. Said optional distillation step will ascertain that the feed to the final product separation is extracting solvent free and water free and the final separation leads to pure and concentrated products. Said optional distillation of said bottom stream preferably takes place at a temperature from about 35 to about 130° C., preferably from about 35 to about 80° C., and most preferably from about 68 to about 75° C., such as about 71° C., at ambient pressure, or optionally at reduced pressure, when the residual 2-methyltetrahydrofuran and water are distilled away. When reduced pressure is used the distillation temperature can be lowered. By said distillation temperature is meant the temperature of the top part of the distillation column.

The bottom stream from said optional distillation comprising the pure formic acid, acetic acid and furfural is preferably further subjected to acid distillation wherein a distillate i.e. top stream, drawn from top part of the acid distillation column, comprising the formic acid and acetic acid and a bottom stream comprising said furfural are obtained. The bottom stream comprising the furfural is preferably further subjected to furfural distillation wherein a stream, comprising furfural is obtained. From the furfural distillation also a distillate comprising residual formic acid and acetic acid drawn from the top part of the column and a stream comprising polymerized furfural and other impurities drawn from the bottom of the column are obtained. The distillate comprising formic acid and acetic is preferably subjected to acetic acid distillation wherein a distillate, drawn from top part of the acetic acid distillation column, comprising concentrated formic acid and a bottom stream comprising concentrated acetic acid are obtained. The distillate comprising formic acid is subjected to formic acid distillation wherein a distillate, drawn from top part of the formic acid distillation column, comprising concentrated formic acid and a bottom stream rich in acetic acid and lean in formic acid are obtained.

In a preferred embodiment the distillate comprising the extractant-water azeotrope from the distillation after extraction is fed to a decanter wherein an upper organic phase comprising essentially extractant and a lower aqueous phase comprising essentially only water are obtained. The organic phase comprising essentially extractant is recycled mainly to the extraction. The aqueous phase comprising essentially only water is combined with aqueous phase from the extraction step and fed to the stripping distillation discussed above. FIG. 1 illustrates one possible schematic layout for a suitable set-up for simultaneously separating and subsequently recovering formic acid, acetic acid and furfural from a dilute aqueous mixture thereof.

Based on the layout of FIG. 1, dilute aqueous mixture 101 comprising formic acid, acetic acid and furfural is fed into an extraction unit 102, which is preferably continuously operating counter-current extraction column, together with fresh 103 and/or recycled 104 extractant. Continuous phase in the extraction can be either aqueous phase or organic phase. In case aqueous phase is the continuous phase the organic phase is the dispersed phase and vice versa. Formed extract 105 comprising formic acid, acetic acid and furfural is recovered. Raffinate 106 comprising essentially water and some dissolved extraction solvent is drawn from the bottom of the extraction unit 102.

Figure 2:
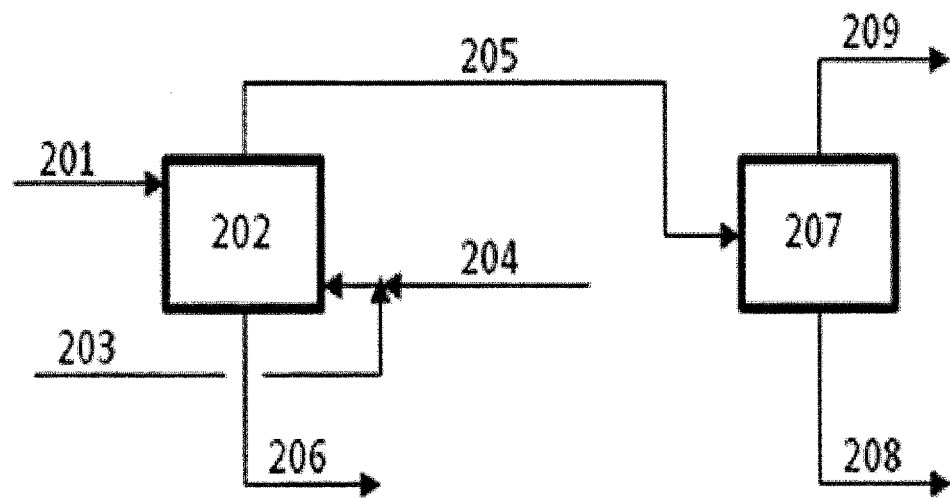
FIG. 2 is a schematic layout set up for a preferred arrangement suitable for use according to the method of the present invention.

In a preferred embodiment of FIG. 2, dilute aqueous mixture 201 comprising formic acid, acetic acid and furfural is fed into an extraction unit 202, which is preferably continuously operating counter-current extraction column, more preferably extraction column comprising of several mixing chambers, most preferably at least 40 mixing chambers each equipped with means for providing efficient or even vigorous mixing such as turbine impellers, together with fresh 203 and/or recycled 204 extractant. Continuous phase in the extraction can be either aqueous phase or organic phase. In case aqueous phase is the continuous phase the organic phase is the dispersed phase and vice versa. Formed extract 205 comprising formic acid, acetic acid, furfural, water and extractant is directed to solvent distillation unit 207 where the extractant and water are distilled. The bottom stream 208 comprising formic acid, acetic acid and furfural is recovered. The distillate 209 i.e. extractant-water azeotrope is drawn from the upper part of the distillation unit 207. The raffinate 206 comprising essentially water is drawn from the bottom of the extraction unit 202.

Figure 3:
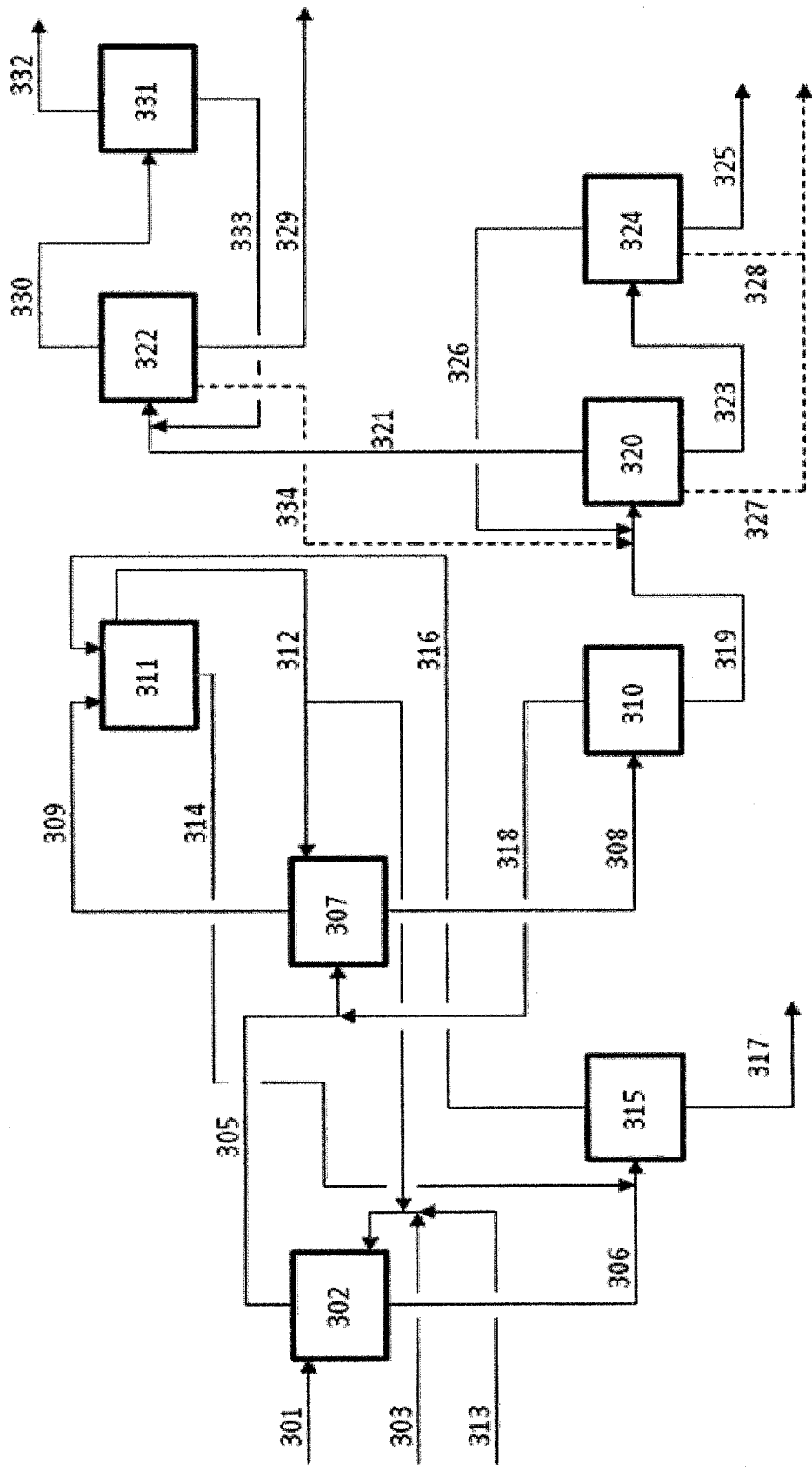
FIG. 3 is a schematic layout set up for another preferred arrangement suitable for use according to the method of the present invention.

In a yet preferred embodiment of FIG. 3, dilute aqueous mixture 301 comprising formic acid, acetic acid and furfural is fed into an extraction unit 302, which is preferably continuously operating counter-current extraction column, together with fresh 303 and/or recycled 312 extractant. Continuous phase in the extraction can be either aqueous phase or organic phase. In case aqueous is the continuous phase then organic phase is the dispersed phase and vice versa. Formed extract 305 comprising formic acid, acetic acid, furfural, water and extractant is directed to solvent distillation unit 307 where the mixture of extractant and water are distilled. The raffinate 306 comprising essentially water is drawn from the bottom of the extraction unit 302. The bottom stream 308 comprising formic acid, acetic acid and furfural and residual solvent and water is optionally directed to solvent distillation unit 310. The distillate 309 i.e. extractant-water azeotrope is drawn from the upper part of the distillation unit 307 and is fed to the decanter 311 wherein the phases are separated, and the organic phase 312 is fed partly back to extraction unit 302 as extractant and partly as reflux to solvent distillation unit 307. Preferably, a small amount of stabilizer solution 313 is dosed to extractant to minimize peroxide formation. The aqueous phase 314 from decanter 311 is combined with raffinate 306 and fed to the top of solvent stripper unit 315 to recover dissolved extractant, which is stripped at ambient pressure as extractant-water azeotropic mixture. The extractant rich distillate 316 from the stripper unit 315 is directed back to decanter 311 for phase separation. Stripper unit bottom stream 317, which is basically pure water and free of extractant is fed to waste disposal or recycled for example to hydrolysis process. The bottom stream 308 of the distillation unit 307 comprises formic acid, acetic acid and furfural, and residual solvent and water. Optionally the residual solvent and water of bottom stream 308 are removed in a solvent residue unit 310 at ambient or reduced pressure and the removed residual solvent and water 318 are recycled back to the feed of solvent distillation unit 307. Bottom stream 319 from unit 310 comprises formic acid, acetic acid and furfural. If the optional unit 310 is not used, the stream 308 is directed directly to acids distillation unit 320. Formic acid and acetic acid are distilled at reduced pressure in the acids distillation unit 320. Formed distillate 321 comprising formic acid and acetic acid are directed to acetic acid distillation unit 322. Furfural rich bottom stream 323 of acids distillation unit 320 is fed to furfural distillation unit 324 operating at reduced pressure, where pure furfural is obtained as product 325. The distillate stream 326 from furfural distillation unit 324 which is rich in formic acid and acetic acid and lean in furfural, is recycled back to acids distillation unit 320. Furfural is prone to polymerization in acidic environment at elevated temperature. Formed polymers and other heavy impurities are removed as purge streams 327 and 328 from the bottom of acids distillation unit 320 and furfural distillation unit 324. The main bottom products are removed as vapor stream above reboiler and condensed. The distillate 321 comprising formic and acetic acid from acids distillation unit 320 is fed to acetic acid distillation unit 322 operating at ambient or reduced pressure, wherein acetic acid 329 is obtained as pure product from the bottom of the acetic acid distillation unit 322. The distillate 330 from the acetic acid distillation unit 322, which is rich in formic acid and lean in acetic acid, is further fed to formic acid distillation unit 331 for the separation of formic acid at ambient or reduced pressure. The distillate 332 from formic acid distillation unit 331 is concentrated formic acid. The bottom stream 333 of formic acid distillation unit 331, which is rich in acetic acid and lean in formic acid, is recycled back to acetic acid distillation unit 322. Possible furfural residues 334 from the acetic acid distillation unit 322 are recycled to acids distillation unit 320.

In the second aspect of the present invention an arrangement for carrying out the method of the present invention is provided. The numbering of the arrangement is referring to FIG. 3.

This arrangement comprises an extraction unit 302, preferably counter current extraction unit, configured to separate the compounds to be recovered, preferably carboxylic acid(s) and furfural, from the diluted aqueous mixture thereof by extraction using an extraction agent, and forming thereby an extract stream 305 and a raffinate stream 306. The arrangement further comprises a distillation unit 307 configured to separate the extracting agent from the compounds to be recovered, preferably carboxylic acid(s) and furfural, by forming a distillate stream 309 and a bottom stream 308, respectively. The stream 308 is directed optionally to a further distillation column 310 from which a bottom stream 319 comprising carboxylic acid(s) and furfural is directed to an acid distillation unit 320 configured to separate the carboxylic acid(s) as the distillate stream 321 from the bottom distillate stream 323 of furfural. If the optional distillation column 310 is not used, the stream 308 is directed directly to the acids distillation unit 320. The stream 321 containing the carboxylic acid(s) is optionally further directed to a further acid distillation unit 322 configured to separate the pure first carboxylic acid 329, preferably acetic acid, from the second carboxylic acid 330, preferably formic acid.

According to a preferred embodiment the arrangement further comprises means for recycling the mixed streams of 306, 309, 316 and 334 to relevant separation phases 315, 311, 311 and 320 to recover the remaining amounts of components to be recovered i.e. preferably formic acid, acetic acid and furfural, or recycled i.e. preferably 2-methyltetrahydrofuran.

In a yet preferred embodiment the arrangement further comprises removal means for streams 327 and 328 comprising the polymerization compound of furfural.

The present invention will be further illustrated by means of the following non-limiting examples.

EXAMPLES

Example 1

Aqueous solution, which contained 3.0 wt-% formic acid (FA), 3.0 wt-% acetic acid (AcOH) and 2.9 wt-% furfural (FUR) was fed to the top part of agitated bench scale Kühni extraction column at the rate of 3.31 kg/h, where it was extracted in a counter-current mode with 2-methyltetrahydrofurane (2-MTHF) fed at the rate of 1.73 kg/h to the lower part of the column. Mass ratio of aqueous to organic feed was 1.91. The diameter of the extraction column was 55 mm and effective height of the column was 1.75 m with 50 mixing chambers each equipped with turbine impeller. The column had a settling zone in the top and bottom part. Organic phase was dispersed into the continuous aqueous phase at the agitation rate of 250 rpm. A clear liquid-liquid interface existed in the upper settling zone. Extraction temperature was 35-45° C. Extract was drawn from the top of the column at the rate of 1.81 g/h. The composition of the extract was 4.1 wt-% formic acid, 4.4 wt-% acetic acid, 5.2 wt-% furfural, 13.2 wt-% water and the rest was 2-MTHF. Raffinate was drawn from the bottom of the extraction column at the rate of 3.23 kg/h and contained 0.8 wt-% formic and 0.6 wt-% acetic acid, 0.0 wt-% furfural, 7.7 wt-% dissolved 2-MTHF and the rest was water. No furfural was detected in the raffinate due to high extractive efficiency of 2-MTHF towards furfural. The extraction yield for formic acid was 74%, acetic acid 80% and furfural 100%.

Table 1 shows material flows (wt-%) of the extraction unit (302) according to FIG. 3.

TABLE 1

| Compound | Feed (Aqueous solution (301)) wt-% | Feed (Extractant (303)) wt-% | Extract (305) wt-% | Raffinate (306) wt-% |
|---|---|---|---|---|
| FA | 3.04 | 0.00 | 4.1 | 0.8 |
| AcOH | 2.97 | 0.00 | 4.4 | 0.6 |
| Furfural | 2.87 | 0.00 | 5.2 | 0.0 |
| Water | 91.12 | 0.00 | 13.2 | 90.9 |
| 2-MTHF | 0 | 100 | 73.1 | 7.7 |

Figure 4:
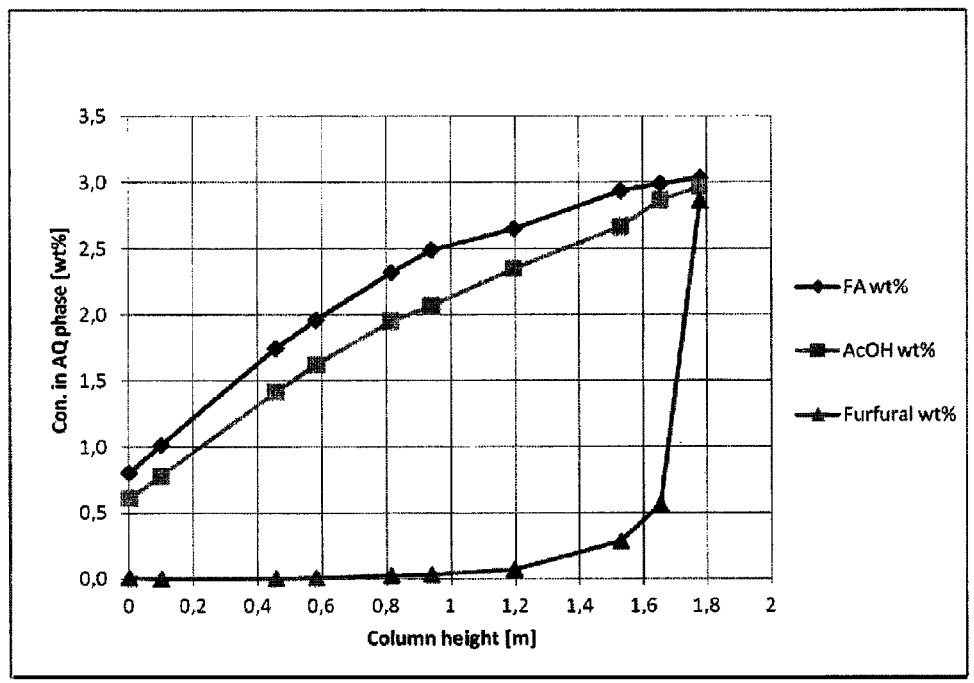
FIG. 4 is a concentration profile of an extraction column (concentration of key components in aqueous phase) when aqueous phase is the continuous phase and organic phase is the dispersed phase.

In FIG. 4 a concentration profile of an extraction column is disclosed wherein aqueous phase is the continuous phase and organic phase is the dispersed phase. The FIG. 4 discloses the concentration of the key components, that is formic acid (FA), acetic acid (AcOH) and furfural in aqueous phase. The extraction is performed with 2-methyltetrahydrofuran in an agitated counter-current column at the agitation rate of 250 rpm. The dilute aqueous solution (feed) contained 3.0 wt-% formic acid, 3.0 wt-% acetic acid and 2.9 wt-% furfural.

Example 2

Aqueous solution, which contained 3.0 wt-% of formic acid (FA), 3.1 wt-% acetic acid (AcOH) and 3.0 wt-% furfural was fed to the top part of agitated bench scale Kühni extraction column at the rate of 3.67 kg/h. It was extracted in a counter-current mode with 2-methyltetrahydrofurane (2-MTHF), which was fed at the rate of 1.88 kg/h to the lower part of the column. In this example 2-MTHF contained 4.7 wt-% water, which mimicked the actual water concentration in recycled extractant. Mass ratio of aqueous to organic feed was 2.1. The diameter of the extraction column was 55 mm and effective height of the column was 1.75 m with 50 mixing chambers each equipped with turbine impeller. The column had a settling zone in the top and bottom part. Aqueous phase was dispersed into continuous organic phase at the agitation rate of 250 rpm. A clear liquid-liquid interface existed in the lower settling zone. Extraction temperature was 35-45° C. Extract was drawn from the top of the column at the rate of 1.96 kg/h. The composition of the extract was 4.7 wt-% formic acid, 5.0 wt-% acetic acid, 5.6 wt-% furfural, 10.7 wt-% water and the rest was 2-MTHF. Raffinate was drawn from the bottom of the column at the rate of 3.59 kg/h and contained 0.52 wt-% formic acid, 0.48 wt-% acetic acid, 0.01 wt-% furfural, 9.5 wt-% dissolved 2-MTHF and the rest was water, and the raffinate was directed to a stripper column. The extraction yield for formic acid was 83%, acetic acid 85% and furfural >99%.

Table 2 shows material flows (wt-%) of the extraction unit (302) according to FIG. 3.

TABLE 2

| Compound | Feed (Aqueous solution (301)) wt-% | Feed (Extractant (303 + 312)) wt-% | Extract (305) wt-% | Raffinate (306) wt-% |
|---|---|---|---|---|
| FA | 3.00 | 0.00 | 4.66 | 0.52 |
| AcOH | 3.13 | 0.00 | 4.98 | 0.48 |
| Furfural | 2.99 | 0.00 | 5.58 | 0.01 |
| Water | 90.88 | 4.65 | 10.65 | 89.45 |
| 2-MTHF | 0 | 95.35 | 74.12 | 9.54 |

Figure 5:
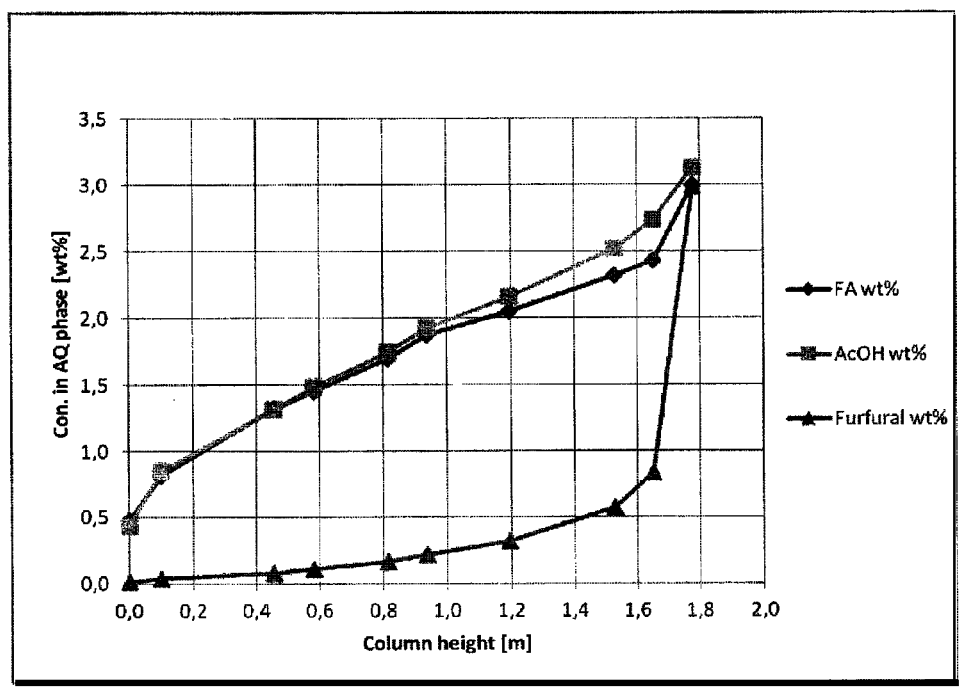
FIG. 5 is a concentration profile of an extraction column profile (concentration of key components in organic phase) when organic phase is the continuous phase and aqueous phase is the dispersed phase.

In FIG. 5 a concentration profile of an extraction column is disclosed wherein organic phase is the continuous phase and aqueous phase is the dispersed phase. The FIG. 5 discloses the concentration of the key components, that is formic acid (FA), acetic acid (AcOH) and furfural in aqueous phase. The extraction is performed with 2-methyltetrahydrofuran in an agitated counter-current column at the agitation rate of 250 rpm. The dilute aqueous solution (feed) contained 3.0 wt-% formic acid, 3.1 wt-% acetic acid and 3.0 wt-% furfural.

Example 3

2-methyltetrahydrofurane (2-MTHF) and dissolved water present in the extract from Example 1 or Example 2 were separated from formic acid, acetic acid and furfural mixture by distillation at ambient pressure. 474 g/h of extract with the analyzed composition of 4.1 wt-% formic acid, 4.7 wt-% acetic acid, 5.8 wt-% furfural, 11.9 wt-% water and the rest was 2-MTHF was fed at 73° C. to the middle of a continuously operating bench distillation column. Column diameter was 30 mm and the total effective height of four sections of structured packing type Sulzer EX was 0.88 m. Distillate vapor i.e. 2-MTHF-water azeotrope was condensed at about 72° C. and directed to a continuously operating decanter. Upper 2-MTHF phase from decanter, which contained 5.1 wt-% of water was split so that part was circulated to extraction at the rate of 360 g/h and part was fed as reflux back to distillation column at the rate of 400 g/h. Column reflux ratio was 1.1 in terms of organic phase. Lower aqueous phase, which contained 7.5 wt-% of 2-MTHF was drawn off from the decanter at the rate of 38 g/h. It was combined with raffinate to recover 2-MTHF in a stripper column. Dark colored bottom stream of the distillation column was drawn off at the rate of 76 g/h at 120° C. With the used distillation conditions bottom stream contained 25.2 wt-% formic acid, 29.2 wt-% acetic acid, 39.1 wt-% furfural, 0.15 wt-% 2-MTHF, 4.2 wt-% water and a small amount of color inducing polymers originating from furfural. Further reduction of residual 2-MTHF and water can be obtained by changing column operating condition or using an additional back-up distillation column.

Table 3 shows material flows (wt-%) of the distillation unit (307) according to FIG. 3.

TABLE 3

| Compound | Feed (extract (305)) wt-% | Distillate (309) wt-% | Bottom stream (308) wt-% |
|---|---|---|---|
| FA | 4.11 | 0.04 | 25.24 |
| AcOH | 4.68 | 0.00 | 29.19 |
| Furfural | 5.80 | 0.00 | 39.07 |
| Water | 11.90 | 9.27 | 4.24 |
| 2-MTHF | 73.51 | 90.69 | 0.15 |
| Polymers | 0 | 0 | 2.11 |

Table 4 shows material flows (wt-%) of the decanter (311) according to FIG. 3.

TABLE 4

| Compound | Feed (distillate (309)) wt-% | Upper, organic, phase (312) wt-% | Lower, aqueous, phase (314) wt-% |
|---|---|---|---|
| FA | 0.04 | 0.01 | 0.70 |
| AcOH | 0.00 | 0.00 | 0.00 |
| Furfural | 0.00 | 0.00 | 0.00 |
| Water | 9.27 | 5.14 | 91.79 |
| 2-MTHF | 90.69 | 94.85 | 7.51 |

Example 4

Residual 2-methyltetrahydrofurane (2-MTHF) was stripped from raffinate from Example 1 or Example 2 and/or Example 3 in a continuously operating stipper column. Raffinate, which contained 9.4 wt-% of 2-MTHF was fed at a rate of 493 g/h to the top of the distillation (stripper) column. 2-MTHF rich distillate was obtained at 71° C. at the rate of 49 g/h. Distillate contained 5.6 wt-% of water. No 2-MTHF was detected in the bottom stream.

Table 5 shows material flows (wt-%) of the stripper unit (315) according to FIG. 3.

TABLE 5

| Compound | Feed (raffinate (306 + 314)) wt-% | Distillate (316) wt-% | Bottom stream (317) wt-% |
|---|---|---|---|
| FA | 0.63 | 0.01 | 0.70 |
| AcOH | 0.69 | 0.00 | 0.75 |
| Furfural | 0.00 | 0.00 | 0.00 |
| Water | 89.30 | 5.63 | 98.55 |
| 2-MTHF | 9.38 | 94.36 | 0.00 |

Example 5

Results of batch extractions of a dilute aqueous mixture with different extractants are disclosed in Tables 6-8. Yields of formic acid (FA), acetic acid (AcOH) and furfural (FUR) transferred to organic phase are disclosed.

In Tables 6 and 7 results of a batch extraction of a dilute aqueous mixture (feed) containing 3.0 wt-% formic acid, 3.0 wt-% acetic acid and 3.0 wt-% furfural in a round bottomed flask are disclosed. Mixing was performed with a propeller and the phases were let to separate. Analyses (HPLC, CE) were made after full separation of the phases. Yields (%) of the components transferred to the organic phase were determined.

TABLE 6

| Extractant | Feed/extractant (g/g) | Temperature (° C.) | Yields (%) | |
|---|---|---|---|---|
| Alamine 336 | 1.4 | 25 | FA | 92 |
| | | | AcOH | 75 |
| | | | FUR | 68 |
| Alamine 304 | 1.5 | 25 | FA | 78 |
| | | | AcOH | 35 |
| | | | FUR | 57 |
| Alamine 336 | 2.1 | 25 | FA | 92 |
| | | | AcOH | 73 |
| | | | FUR | 67 |

TABLE 6-continued

| Extractant | Feed/extractant (g/g) | Temperature (° C.) | Yields (%) | |
|---|---|---|---|---|
| Alamine 336 | 4.2 | 25 | FA | 91 |
| | | | AcOH | 67 |
| | | | FUR | 64 |
| 2-MTHF | 1.4 | 40 | FA | 39 |
| | | | AcOH | 45 |
| | | | FUR | 74 |
| 2-MTHF | 2.2 | 40 | FA | 28 |
| | | | AcOH | 36 |
| | | | FUR | 73 |
| 2-MTHF | 3.5 | 25 | FA | 22 |
| | | | AcOH | 17 |
| | | | FUR | 53 |
| 2-MTHF | 4.2 | 40 | FA | 18 |
| | | | AcOH | 22 |
| | | | FUR | 56 |

Alamine 304 = tri(dodecyl) amine
Alamine 336 = tri(octyl/decyl) amine
2-MTHF = 2-methyltetrahydrofuran High boiling Alamine 336 and low boiling 2-MTHF were able to extract all the components of the 3-3-3 (wt-%) mixture. Alamine 336 forms complexes with the acids, 2-MTHF just dissolves them.

TABLE 7

| Extractant | Feed/extractant (g/g) | Temperature (° C.) | Yields (%) | |
|---|---|---|---|---|
| MIBK | 1.0 | 25 | FA | 31 |
| | | | AcOH | 37 |
| | | | FUR | 91 |
| 2-MTHF | 1.0 | 25 | FA | 59 |
| | | | AcOH | 64 |
| | | | FUR | 89 |
| 2-MTHF | 1.0 | 50 | FA | 57 |
| | | | AcOH | 62 |
| | | | FUR | 86 |

MIBK = methyl isobutylketone (a polar neutral O solvent like 2-MTHF)

Ketones are good extractants for furfural but less efficient for formic acid and acetic acid when compared with 2-MTHF. When the amount of 2-MTHF is high (feed/extractant=1), increase of temperature from 25 to 50° C. has no practical effect on extraction of formic acid, acetic acid and furfural but the amount of 2-MTHF dissolved in raffinate is halved.

In Table 8 results of a batch extraction of a dilute aqueous mixture (feed) containing only 3.0 wt-% furfural in a round bottomed flask are disclosed. Mixing was performed with a propeller and the phases were let to separate. Analyses (HPLC, CE) were made after full separation of the phases. Yield (%) of the component transferred to the organic phase was determined.

TABLE 8

| Extractant | Feed/extractant (g/g) | Temperature (° C.) | Yields (%) | |
|---|---|---|---|---|
| Alamine 336 | 4.2 | 25 | FUR | 4 |
| Cyclohexane | 2.2 | 25 | FUR | 29 |
| Diethylbenzenes | 2.2 | 25 | FUR | 62 |
| 2-MTHF | 2.2 | 25 | FUR | 78 |

Without acids in the feed, Alamine 336 behaves like n-alkanes, which are very poor extractants for all components in a dilute aqueous mixture containing 3.0 wt-% formic acid, 3.0 wt-% acetic acid and 3.0 wt-% furfural.

The invention claimed is:

1. A method for separating at least one carboxylic acid and furfural simultaneously from a dilute aqueous mixture wherein the total concentration of the carboxylic acids is less than 20% by weight and which further contains as impurities light water soluble polar compounds and/or light hydrocarbons, wherein the method comprises subjecting the dilute aqueous mixture to extraction with at least one methyltetrahydrofuran selected from the group of monomethyltetrahydrofuran and dimethyltetrahydrofuran, forming an extract comprising an organic phase and a raffinate comprising an aqueous phase, and recovering from the extract the at least one carboxylic acid and furfural.

2. The method according to claim 1 wherein recovering of the at least one carboxylic acid and furfural comprises subjecting the extract to distillation whereby are obtained a distillate, which is withdrawn from a top part of the distillation column and which is comprising an extractant-water azeotrope, and a bottom stream, which is comprising essentially the at least one carboxylic acid and furfural.

3. The method according to claim 2 wherein the bottom stream comprising essentially the at least one carboxylic acid and furfural is subjected to a further distillation whereby are obtained a distillate, withdrawn from a top part of the further distillation column, comprising water and methyltetrahydrofuran, and a further bottom stream, comprising the at least one carboxylic acid and furfural.

4. The method according to claim 1 wherein the methyltetrahydrofuran is 2-methyltetrahydrofuran.

5. The method according to claim 1 wherein the at least one carboxylic acid is a lower aliphatic carboxylic acid or mixtures thereof.

6. The method according to claim 5 wherein the lower aliphatic carboxylic acid is selected from the group of formic acid and acetic acid.

7. The method according to claim 1 wherein the total carboxylic acid concentration in the dilute aqueous mixture is less than 15% by weight.

8. The method according to claim 7 wherein the total carboxylic acid concentration in the dilute aqueous mixture is in the range from 0.1 to 10% by weight.

9. The method according to claim 7 wherein the total carboxylic acid concentration in the dilute aqueous mixture is in the range from 0.5 to 5% by weight.

10. The method according to claim 1 wherein the furfural concentration of the dilute aqueous mixture is less than 40% by weight.

11. The method according to claim 10 wherein the furfural concentration of the dilute aqueous mixture is less than 15% by weight.

12. The method according to claim 10 wherein the furfural concentration of the dilute aqueous mixture is in the range from 0.01 to 10% weight.

13. The method according to claim 1 wherein the dilute aqueous mixture originates from biomass.

14. The method according to claim 1 wherein the dilute aqueous mixture originates from a biomass hydrolysis process.

15. The method according to claim 1 wherein the dilute aqueous mixture originates from an acidic biomass hydrolysis process to produce at least one of levulinic acid and the esters thereof.

16. The method according to claim 1 wherein the extraction takes place at a temperature from about 10° C. to about 80° C. and under a pressure of at most 5 bar.

17. The method according to claim 2 wherein the distillation of the extract takes place at a temperature of about 35° C. to about 110° C.

18. The method according to claim 2 wherein the distillation of the extract takes place under ambient pressure.

19. The method according to claim 3 wherein the second distillation of the bottom stream takes place at a temperature from about 35° C. to about 130° C.

20. The method according to claim 3 wherein the second distillation of the bottom stream takes place under a pressure selected from ambient and reduced pressure.

21. The method according to claim 1 wherein the mass ratio of dilute aqueous mixture to methyltetrahydrofuran in the feed is from about 0.25 to about 4.

22. The method according to claim 2 wherein the bottom stream comprising the at least one carboxylic acid and furfural is subjected to acid distillation wherein are obtained a distillate, drawn from a top part of the acid distillation column, comprising the at least one carboxylic acid, and a bottom stream comprising the furfural.

23. The method according to claim 3 wherein the further bottom stream comprising the at least one carboxylic acid and furfural is subjected to acid distillation wherein are obtained a distillate, drawn from a top part of the acid distillation column, comprising the at least one carboxylic acid, and a bottom stream comprising the furfural.

\* \* \* \* \*